United States Patent [19]

Takase et al.

[11] Patent Number: 4,595,694
[45] Date of Patent: Jun. 17, 1986

[54] AZULENE DERIVATIVES, PROCESSES OF THEIR SYNTHESIS AND THEIR USES AS ANTI-ULCERATIVE AND ANTI-INFLAMMATORY AGENTS

[75] Inventors: Kahei Takase; Masafumi Yasunami, both of Sendai; Tsuyoshi Tomiyama, Sakaki; Akira Tomiyama, Togura; Takashi Yanagisawa, Sakaki, all of Japan

[73] Assignee: Kotobuki Seiyaku Co. Ltd., Nagano, Japan

[21] Appl. No.: 642,043

[22] Filed: Aug. 17, 1984

[30] Foreign Application Priority Data

Aug. 24, 1983 [JP] Japan .................................. 58-153187
Jan. 28, 1984 [JP] Japan .................................. 59-014028

[51] Int. Cl.$^4$ ................................................ C07F 5/06
[52] U.S. Cl. ..................................... 514/492; 260/503; 556/177
[58] Field of Search ........................... 260/503, 448 R; 514/492; 556/177

[56] References Cited

U.S. PATENT DOCUMENTS 3,974,299  8/1976  Crosby et al. ............... 260/448 R X
4,224,240  9/1980  Kane et al. ........................... 260/503
4,283,347  8/1981  Kane et al. ................. 260/448 R X

OTHER PUBLICATIONS

Chemical Abstracts 88 115068n (1976).
Chemical Abstracts 88 130698m (1976).

*Primary Examiner*—Helen M. S. Sneed
*Attorney, Agent, or Firm*—Robert E. Burns; Emmanuel J. Lobato; Bruce L. Adams

[57] ABSTRACT

A new series of azulene derivatives are disclosed. These compounds are stable to light and heat and are useful as anti-ulcerative and anti-inflammatory agents. Such compounds can be synthesized by reacting 2H-cyclohepta(b) furan-2-one or its derivative substituted by a lower alkyl with a suitable enamine derived from a corresponding aldehyde or ketone, and then sulfonating the compound resulting from said reaction.

12 Claims, No Drawings

AZULENE DERIVATIVES, PROCESSES OF THEIR SYNTHESIS AND THEIR USES AS ANTI-ULCERATIVE AND ANTI-INFLAMMATORY AGENTS

BACKGROUND OF THE INVENTION

This invention relates to new chemical compounds having valuable therapeutic properties and methods of synthesizing them.

Azulene derivatives have been well known as having anti-gastric ulcer, anti-gastritis and anti-inflammation activities. However, because of their instability against light and heat, an improved stable and potent derivative has been long desired.

SUMMARY OF THE INVENTION

The principal object of the present invention is the provision of novel compounds having advantageous pharmaceutical properties.

Another object of the present invention is the provision of pharmaceutical compositions useful as anti-peptic ulcerative agents.

Another important object of the present invention is the provision of pharmaceutical compositions useful as anti-inflammatory agents.

Still another object of the present invention is the provision of the sodium sulfonate of new azulene derivatives and a method for the manufacture thereof.

These and other objects of the invention will become apparent from the description that follows.

DETAILED DESCRIPTION OF THE INVENTION

The compounds of this invention are shown by the general formula I

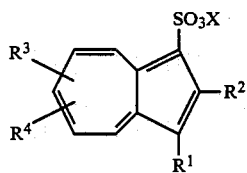

wherein $R^1$ is a lower alkyl, benzyl, or

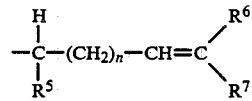

group in which $R^5$, $R^6$, $R^7$ each represents H or a lower alkyl group and n is 1 or 2, $R^2$ and $R^3$ are H or a lower alkyl, $R^4$ is H or an alkyloxy group, and X is Na or $Al(OH)_2$.

The compounds indicated by the general formula I possess a potent anti-gastric ulcerative and anti-inflammatory activity, therefore, they are regarded as therapeutically useful. For this purpose, sodium guaiazulene-3-sulfonate has heretofore been used. The compounds of this invention are more potent and chemically stable then the aforegoing compound.

The lower alkyl groups which are shown as $R^1$, $R^2$, $R^3$, $R^4$, $R^5$, $R^6$ and $R^7$ in the general formula I mean straight chain alkyl group or branched alkyl groups having from 1 to 6 carbon atoms. Such compounds are desirable when the positions of substituents $R^3$ and $R^4$ are at the 4, 6 or 7 position of the seven membered ring of general formula I.

The following compounds of the invention are of particular interest.

(1) Sodium 3-methyl-azulene sulfonate.
(2) Sodium 3-ethyl-azulene sulfonate.
(3) Sodium 3-ethyl-7-isopropyl-azulene sulfonate.
(4) Sodium 3-ethyl-6-isopropyl-azulene sulfonate.
(5) Sodium 3-(1'-R, S-1',5'-dimethyl-4'-hexene) azulene sulfonate.
(6) Sodium 3-n-butyl-azulene sulfonate.
(7) Sodium 3-methyl-2-ethyl-azulene sulfonate.
(8) Sodium 3-(1'-S-1',5'-dimethyl-4'-hexene)-azulene sulfonate.
(9) Sodium 3-(1'-R-1',5'-dimethyl-4'-hexene)-azulene sulfonate.
(10) Sodium 3-(1'-S-1',5'-dimethyl-4'-hexene)-7-isopropyl-azulene sulfonate.
(11) Sodium 3-(1'-R-1',5'-dimethyl-4'-hexene)-7-isopropyl-azulene sulfonate.
(12) Sodium 3-propyl-azulene sulfonate.
(13) Sodium 3-methyl-7-isopropyl-azulene sulfonate.
(14) Sodium 3-n-butyl-azulene sulfonate.
(15) Sodium 3-n-pentyl-azulene sulfonate.
(16) Sodium 5-isopropyl-azulene sulfonate.
(17) Sodium 7-isopropyl-3-n-propyl-azulene sulfonate.
(18) Sodium 7-isopropyl-3-n-butyl-azulene sulfonate.
(19) Sodium 7-isopropyl-3-n-pentyl-azulene sulfonate.
(20) Sodium 7-isopropyl-3-(1'-R, S-1',5'-dimethyl-4'-hexene)-azulene sulfonate.
(21) Sodium 7-isopropyl-3-(1'-R-1',5'-dimethyl-4'-hexene)-azulene sulfonate.
(22) Sodium 7-isopropyl-3-(1'-S-1',5=-dimethyl-4'-hexene)-azulene sulfonate.
(23) Sodium 7-isopropyl-3-benzyl-azulene sulfonate.
(24) Sodium 4-methoxy-3-methyl-azulene sulfonate.
(25) Sodium 4-methoxy-3-ethyl-azulene sulfonate.
(26) Sodium 4-methoxy-3-propyl-azulene sulfonate.
(27) Sodium 4-methoxy-3-butyl-azulene sulfonate.
(28) Sodium 4-methoxy-3-pentyl-azulene sulfonate.
(29) Sodium 4-methoxy-3-hexyl-azulene sulfonate.
(30) Sodium 7-isopropyl-4-methoxy-3-methyl-azulene sulfonate.
(31) Sodium 7-isopropyl-4-methoxy-3-ethyl-azulene sulfonate.
(32) Sodium 7-isopropyl-4-methoxy-3-propyl-azulene sulfonate.
(33) Sodium 7-isopropyl-4-methoxy-3-butyl-azulene sulfonate.
(34) Sodium 7-isopropyl-4-methoxy-3-pentyl-azulene sulfonate.
(35) 3-methyl-azulene sulfonic acid aluminum salt.
(36) 3-ethyl-azulene sulfonic acid aluminum salt.
(37) 7-isopropyl-3-methyl-azulene sulfonic acid aluminum salt.
(38) 7-isopropyl-3-ethyl-azulene sulfonic acid aluminum salt.

The above-mentioned compounds numbered from 1 to 38, will be referred to hereinafter, as compound 1, compound 2, . . . , compound 38, respectively.

The new azulene derivatives of general formula (I) are obtained by sulfonation of the compound shown by the general formula (II) for conversion to a sodium or aluminum salts

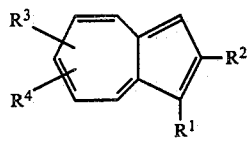

(II)

(The symbols are already shown hereinbefore)

The pre-sulfonated compounds indicated by the formula (II) are prepared by several ways as below.

(i) The compounds in which $R^1$ and $R^3$ are H or a lower alkyl and $R^2$ is H, are obtained by the method according to L. T. Scott (J. Am. Chem. Soc. 102 6311p 1980) or M. Yasunami (Chemistry Letters 579p 1980), one of the inventors of this invention.

(ii) In case of $R^1$ is

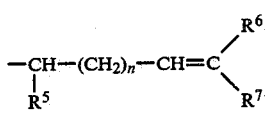

or benzyl, the objective compound is obtained by reacting 2H-cyclohepta(b)furan-2-one with an enamine obtained from corresponding aldehydes of the formula: $R^1$—$CH_2CHO$, according to M. Yasunami (Chem. Lett. 579p 1980).

(iii) To obtain compounds in which both $R^1$ and $R^2$ are lower alkyls, the same process as that of (ii) is applied using an enamine obtained from a ketone

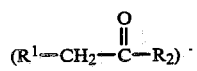

instead of an aldehyde ($R^1$—$CH_2CHO$), in reaction (ii), even though the starting aldehyde contains a sterospecific isomer, for example, $R^1$ is d- or l-citronellal and d- or l-limonene, the resulting product is found to keep its stereospecificity.

(iv) The other compounds are also prepared according to M. Yasunami (Chem. Lett. 579p 1980).

The compounds obtained as mentioned above are purified by distillation under reduced pressure or column chromatography and then submitted to sulfonation. Sulfonation is generally carried out in acetic anhydride by adding sulfuric acid with cooling; also in other cases, sulfuric anhydride-pyridine complex can be utilized. The resulting sulfonated compound is converted to its sodium salt with a sodium hydroxide solution or sodium ethylate and then recrystallized from alcohols.

To obtain aluminum salts, sodium sulfonates are converted by aluminum salt solution, for example, a water solution of $Al(OH)_3$, $AlCl_3$ or aluminum propoxide.

The compounds of this invention thus obtained possess improved stability to light and heat and some of these compounds have excellent anti-peptic and anti-gastric ulcer activity and are promising for therapeutic use. The following examples show biological activity as compared with sodium guaizulene-3-sulfonate (GAS) as a standard drug, the preparation of typical comopsition of the present invention and the process to synthesize them.

PHARMACOLOGICAL DATA 1

Anti-peptic activity of the compounds is tested in vitro according to V. K. Thiemer (Arznei-Forsch 22 (6), PP. 1086, 1972), using bovine serum albumin as a substrate and commercially available pepsin.

Activity is expressed as % inhibition to the control value (no inhibitor added) as shown in table 1. Also $ID_{50}$ (50% inhibiting dose) is obtained graphically.

TABLE 1

| | % inhibition sample | | | |
|---|---|---|---|---|
| concentration (mg/ml) | compound 3 | compound 4 | compound 5 | GAS |
| 0.125 | 17.304 | 17.305 | 0.260 | 14.578 |
| 0.250 | 47.596 | 28.864 | 3.570 | 50.357 |
| 0.500 | 63.570 | 65.747 | 24.480 | 58.604 |
| 1.000 | 97.142 | 55.844 | 50.356 | 75.130 |
| $ID_{50}$ (mg/ml) | 0.297 | 0.510 | 1.207 | 0.358 |

$ID_{50}$: 50% inhibition doses

PHARMACOLOGICAL DATA 2

In order to ascertain the anti-ulcerative activity in vitro, Shay's rat (Gastro enterology 26, P. 906) is selected. Rats are fasted for 48 hours and pylorus ligation is carried out under light anesthesia. Drug is given perorally. 16 hours after ligation the animals are sacrificed and the stomach is removed. The induced erosion is measured in area and scored as ulcer index (U.I.). The data are expressed as % inhibition to the control value from the equation described below.

$$\% \text{ inhibition} = \frac{\text{control value} - \text{test value}}{\text{control value}} \times 100$$

| test compound | dose (mg/kg) | % inhibition |
|---|---|---|
| compound 1 | 500 mg | 52.4 |
| compound 2 | " | 100 |
| compound 3 | " | 100 |
| compound 4 | " | 100 |
| compound 5 | " | 95.5 |
| compound 8 | " | 69.9 |
| compound 12 | 100 | 78.5 |
| compound 13 | " | 69.7 |
| compound 14 | " | 32.7 |
| compound 15 | " | 64.3 |
| compound 16 | " | 62.0 |
| compound 17 | " | 31.2 |
| compound 18 | " | 17.2 |
| compound 19 | " | −56.3 |
| compound 20 | " | 43.8 |
| compound 21 | " | 14.5 |
| compound 22 | " | −19.5 |
| compound 23 | " | 9.8 |
| compound 24 | " | 63.4 |
| compound 25 | " | 75.6 |
| compound 26 | " | 75.6 |
| compound 27 | " | 66.3 |
| compound 28 | " | 42.0 |
| compound 29 | " | 38.0 |
| compound 30 | " | 58.7 |
| compound 31 | " | 67.6 |
| compound 32 | " | 44.1 |
| compound 33 | " | 64.8 |
| compound 34 | " | −14.6 |
| compound 35 | " | 16.5 |
| compound 36 | " | 28.6 |
| compound 37 | " | 58.4 |
| compound 38 | " | 40.3 |

TOXICITY

The acute toxicity of Compound 3 is determined by Litchfield & Wilcoxon method using SD rats.

The $LD_{50}$ values of the compound is shown below.

| | LD$_{50}$ VALUE (mg/kg) | |
|---|---|---|
| Administration route | ♂ | ♀ |
| P.O. | 1000(833.3–1200) | 1200(983.6–145.4) |
| I.P. | 165(136.4–199.8) | 180(153.8–210.6) |
| I.V. | 130 | 153(111.7–209.6) |
| | (95% confidence limits) | |

It should be emphasized that stability of the compound 3 is greatly improved compared with that of sodium guaiazulene sulfonate which has been used clinically until now.

Because the instability of sodium guaiazulene sulfonate has limited its pharmaceutical utility, the improved stability of the compounds of this invention will be an another merit of this compound.

The following data show the stability of this compound. The data are expressed in % residue of the original compounds after the storage in each condition.

| | storage | | | |
|---|---|---|---|---|
| | 40° C. 96 hours | 60° C. 192 hours | 70° C. 240 hours | 80° C. 288 hours |
| sodium guaiazulene sulfonate | 100% | 51.3% | 9.3% | 1.5% |
| compound 3 | 100% | 100% | 100% | 100% |

For pharmaceutical purpose, the compounds of the present invention are administered to animals and human perorally, parenterally or rectally as active ingredients in customary dosage unit composition, that is, compositions in dosage unit form consisting essentially of an inert pharmaceutical carrier and one effective dosage unit of the active ingredient, such as tablets, granules, capsules, suspensions and the like. One effective dosage unit of the compounds according to the present invention is from 2 mg. to 60 mg., 3 times a day for an adult.

The following examples illustrate typical pharmaceutical dosage unit compositions comprising a compound of the present invention as an active ingredient and represent the modes contemplated of putting the invention into practical use. PHARMACEUTICAL EXAMPLE 1

Granules with following ingredients

| Sodium 3-ethyl-7-isopropyl-azulene sulfonate | 3 mg |
|---|---|
| Lactose | 433 mg |
| L-glutamine | 60 mg |
| Methyl cullulose | 4 mg |
| total | 500 mg |

Preparation

The ingredients are intimately admixed with each other, the mixture is granulated in a conventional manner.

PHARMACEUTICAL EXAMPLE 2

Granules with following ingredients

| Sodium 3-ethyl-7-isopropyl-azulene sulfonate | 6 mg |
|---|---|
| Lactose | 430 mg |
| L-glutamine | 60 mg |
| Methyl cellulose | 4 mg |
| total | 500 mg |

PHARMACEUTICAL EXAMPLE 3

Granules with following ingredients

| Sodium 3-ethyl-7-isopropyl-azulene sulfonate | 9 mg |
|---|---|
| Lactose | 427 mg |
| L-glutamine | 60 mg |
| Methyl cellulose | 4 mg |
| total | 500 mg |

PHARMACEUTICAL EXAMPLE 4

Granules with following ingredients

| Sodium 3-ethyl-7-isopropyl-azulene sulfornate | 3 mg |
|---|---|
| Lactose | 393 mg |
| Synthetic hydrotalcite | 100 mg |
| Methyl cellulose | 4 mg |
| total | 500 mg |

PHARMACEUTICAL EXAMPLE 5

Granules with following ingredients

| Sodium 3-ethyl-7-isopropyl-azulene sulfonate | 6 mg |
|---|---|
| Lactose | 390 mg |
| Synthetic hydrotalcite | 100 mg |
| Methyl cellulose | 4 mg |
| total | 500 mg |

PHARMACEUTICAL EXAMPLE 6

Granules with following ingredients

| Sodium 3-ethyl-7-isopropyl-azulene sulfonate | 9 mg |
|---|---|
| Lactose | 287 mg |
| Synthetic hydrotalcite | 100 mg |
| Methyl cellulose | 4 mg |
| total | 500 mg |

PHARMACEUTICAL EXAMPLE 7

Granules with following ingredients

| Sodium 3-ethyl-7-isopropyl-azulene sulfonate | 3 mg |
|---|---|
| Lactose | 150 mg |
| Starch | 343 mg |
| Methyl cellulose | 4 mg |
| total | 500 mg |

PHARMACEUTICAL EXAMPLE 8

Granules with following ingredients

| Sodium 3-ethyl-7-isopropyl-azulene sulfonate | 6 mg |
|---|---|
| Lactose | 150 mg |
| Starch | 340 mg |
| Methyl cellulose | 4 mg |
| total | 500 mg |

PHARMACEUTICAL EXAMPLE 9

Granules with following ingredients

| | |
|---|---|
| Sodium 3-ethyl-7-isopropyl-azulene sulfonate | 9 mg |
| Lactose | 150 mg |
| Starch | 337 mg |
| Methyl cellulose | 4 mg |
| total | 500 mg |

Any of the other compounds embraced in formula I may be substituted for the particular active ingredient in the above Pharmaceutical Examples 1–9. Likewise, the amount of active ingredient in these illustrative pharmaceutical examples may be varied to achieve the dosage unit range set forth above, and the amounts and nature of the inert pharmaceutical carrier ingredients may be varied to meet particular requirements. While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

EXAMPLE 1

Sodium 1-methyl-azulene-3-sulfonate

The starting compound, 1-methylazulene, can be prepared as illustrated below according to Yasunami et al (Chemistry Letters, pp. 579–582, 1980).

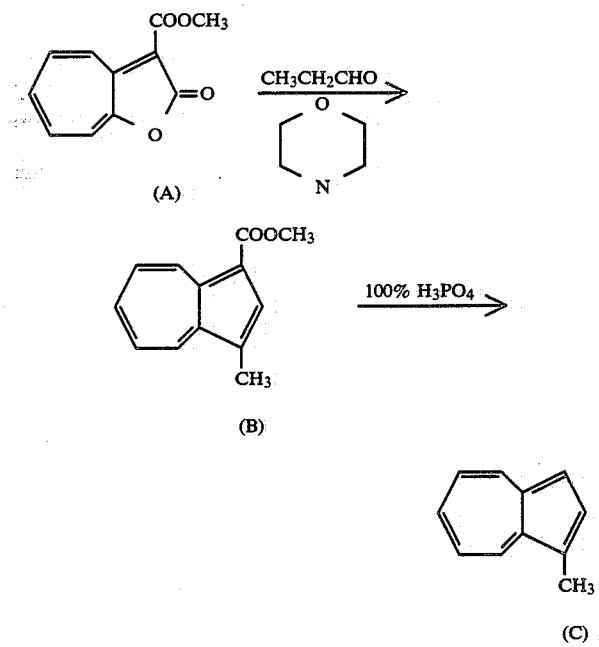

Step 1

1-methyl-3-carboxymethylazulene (B)

A solution of oxazulene (A) 6 g. propionaldehyde 5.22 g. and morpholine 7.84 g. in 120 ml. of EtOH is refluxed for 4 hours. The mixture is cooled and the organic solvent is removed under reduced pressure. The residue is extracted with benzene and the organic layer is washed with water and dried.

After removal of benzene, the residue is applied to silicagel column chromatography using benzene as eluent to give 5.9 g. of product in solid after removal of solvent.

Yield: 5.9 g (98.5%).

mp: 69°–71° C.

ir: 2950, 1690, 1450, 1440, 1421, 1202, 1027, 774, 746 (cm$^{-1}$)

$^1$H-NMR: (CDCl$_3$) 2.58(3H, S, Me), 3.92(3H, S, OMe), 7.28 (1H, dd, J=9.6, 96, H-5), 7.37 (1H, dd, J=9.6, 9.6, H-7), 7.67 (1H, dd, J=9.6, 9.6, H-6), 8.14 (1H, S, H-2), 8.24 (1H, dd, J=9.6, 1.4, H-4), 9.49 (1H, dd, J=9.6, 1.4, H-8).

Step 2

1-methylazulene (C)

5.91 g of compound B is dissolved in 60 ml. of phosphoric acid and the mixture is heated (90°–80° C.) on a water bath for 15 minutes. After cooling the mixture is poured into 300 ml of ice-water and extracted with n-hexane. The organic layer is separated, washed with water, dried over anhydrous sodium sulfonate and fractionated by silicagel column chromatography using benzene as eluent to give 3.72 g (90.1%) of the objective compound.

ir: 3012, 2930, 1577, 1510, 1455, 1396, 947, 880 (cm$^{-1}$).

$^1$H-NMR: (CDCl$_3$) 2.58(3H, S, Me), 3.92(3H, S, OMe), 7.28 (1H, dd, J=9.6, 9.6, H-5), 7.37 (1H, dd, J=9.6, 9.6, H-7), 7.67 (1H, dd, J=9.6, 9.6, H-6), 8.14 (1H, S, H-2), 8.24 (1H, dd, I=9.6, 1.4, H-4), 9.49 (1H, dd, J=9.6, 1.4, H-8).

Step 3

Sodium 3-methyl-azulene sulfonate (compound 1)

Acetic anhydride in an amount of 10 ml is added to 1.0 g. of 1-methylazulene under cooling with ice-water, sulfuric acid in an amount of 3.4 g. is added dropwise and the reaction mixture is stirred for 4 hours at 0° C. Then, the reaction mixture is alkalized to pH8–9 by adding 40% of sodium hydroxide solution and the generated solid is collected and dried. The product is recrystalized from 95% ethanol to give 1.1 g. of the objective compound.

mp: 35°–38° C.

ir: 1630, 1420, 1220, 750 (cm$^{-1}$)

Compounds 2–34 are obtained by the same sulfonating procedure as above mentioned Step 3 from corresponding starting materials which have been disclosed in the literature (M. Yasunami, Chem. lett., p.579, 1980).

EXAMPLE 2

Sodium 3-ethyl-azulene sulfonate (compound 2)

Compound 2 is obtained by using n-butylaldehyde instead of propionaldehyde in Step 1 of Example 1.

mp: 28°–30° C.

ir: 1630, 1425, 1400, 1220, 850 (cm$^{-1}$)

EXAMPLE 3

Sodium 3-ethyl-7-isopropyl-azulene sulfonate (compound 3)

Compound 3 is prepared by following the procedures of example 1, using the 5-isopropyl-substituted derivative of oxazulene as a starting material instead of oxazulene (A) and n-butyraldehyde instead of propionaldehyde. The sulfonation is carried out according to the procedures of Step 3 of Example 1.
mp: 85°–88° C.
ir: 1650, 1640, 1565, 1418, 1180, 1050 (cm$^{-1}$)
$^1$H-NMR (DMSO): 1.30 (3H, t, J=7.4, CH$_3$), 1.33 (6H, d, J=6.6, (CH$_3$)$_2$—), 3.00 (2H, q, J=7.4, CH$_2$), 3.50 (1H, sept, J=6.6, —CH—(CH$_3$)$_2$), 4.10 (1H, bs, H$_2$O), 7.20 (1H, d, J=10, H-7), 7.90 (1H, s, H-2), 8.23 (1H, d, J=10, H-4), 9.17 (1H, s, H-8)

EXAMPLE 4

Sodium 3-ethyl-6-isopropyl-azulene sulfonate (compound 4)

mp: 55°–58° C.
ir: 1640, 1580, 1410, 1190, 1060 (cm$^{-1}$)
$^1$H-NMR (DMSO): 1.27 (3H, t, J=7.4, CH$_3$), 1.30 (6H, d, J=6.6, (CH$_3$)$_2$—), 2.96 (1H, sept, J=6.6, isopropyl), 3.02 (2H, q, J=7.4, CH$_2$), 7.17 (2H, d, J=10, H-5,7), 7.70 (1H, s, H-2), 8.20 (1H, d, J=10, H-8), 8.90 (1H, d, J=10, H-4).

EXAMPLE 5

Sodium 3-(1'-R, S-1'-5'-dimethyl-4-hexene)-azulene sulfonate (compound 5)

Compound 5 is prepared according to Example 1, using d.1-citronellal instead of propionaldehyde in Exampe 1.
mp: 78°–81° C.
ir: 1630, 1560, 1420, 1400, 1190, 1120, 1050, 750 (cm$^{-1}$)

EXAMPLE 6

Sodium 3-n-butyl-azulene sulfonate (compound 6)

mp: 83°–85° C.
ir: 1630, 1420, 1400, 1220, 750 (cm$^{-1}$)

EXAMPLE 7

Sodium 3-methyl-2-ethyl-azulene sulfonate (compound 7)

Compound 7 is prepared according to Example 1, using 3-(1-pyrrolidinyl)-2-pentene instead of propionaldehyde and morpholine in Step 1 of Example 1.
mp: 280°–283° C.
ir: 1640, 1560, 1420, 1190, 1040, 740 (cm$^{-1}$)

EXAMPLE 8

Sodium 3-(1'-S-1',5'-dimethyl-4'-hexene)-azulene sulfonate (compound 8)

Compound 8 is prepared according to Example 1, using d-citronellal instead of propionaldehyde in Step 1 of Example 1.
mp: 78°–81° C.
ir: 1630, 1560, 1420, 1400, 1190, 1120, 1050, 750 (cm$^{-1}$)

EXAMPLE 9

Sodium 3-(1'-R-1',5'-dimethyl-4'-hexene)-azulene sulfonate (compound 9)

Compound 9 is prepared according to Example 1, using l-citronellal instead of propionaldehyde in Step 1 of Example 1.
mp: 78°–81° C.
ir: 1630, 1560, 1420, 1400, 1190, 1120, 1050, 750 (cm$^{-1}$)

EXAMPLE 10

Sodium 3-(1'-S-1',5'-dimethyl-4'-hexene)-7-isopropyl-azulene sulfonate (compound 10)

mp: 108°–110° C.
ir: 1630, 1560, 1420, 1220, 1050 (cm$^{-1}$).

EXAMPLE 11

Sodium 3-(1'-R-1',5'-dimethyl-4'-hexene)-7-isopropyl-azulene sulfonate (compound 11)

mp: 108°–110° C.
ir: 1630, 1560, 1420, 1220, 1050 (cm$^{-1}$).

EXAMPLE 12

Sodium 3-propylazulene sulfonate (compound 12)

mp: 210°–215° C. (decomp.) ("decomp." stands for decomposition point, hereinafter.)
ir: 3400, 2940, 2850, 1580, 1420, 1400, 1200, 1090, 1020, 960, 880, 750, 740, 670 (cm$^{-1}$)

EXAMPLE 13

Sodium 3-methyl-4-isopropylazulene sulfonate (compound 13)

mp: 91°–93° C.
ir: 3450, 2950, 1640, 1250, 1070, 1010, 790 (cm$^{-1}$)

EXAMPLE 14

Sodium 3-n-butylazulene sulfonate (compound 14)

mp: 215°–220° C. (decomposition point).
ir: 3450, 2900, 1570, 1390, 1190 (cm$^{-1}$)

EXAMPLE 15

Sodium 3-n-pentylazulene sulfonate (compound 15)

mp: 217°–220° C. (decomp.).
ir: 3450, 2900, 1570, 1390, 1190 (cm$^{-1}$).

EXAMPLE 16

Sodium, 5-isopropylazulene sulfonate (compound 16)

mp: 214°–248° C.
ir: 3450, 2950, 1640, 1200, 1050 (cm$^{-1}$)

EXAMPLE 17

Sodium 7-isopropyl-3-n-propylazulene sulfonate (compound 17)

mp: 138°–143° C.
ir: 3450, 2950, 1630, 1575, 1470, 1415, 1390, 1220, 1050, 930 (cm$^{-1}$)

EXAMPLE 18

Sodium 7-isopropyl-3-n-butylazulene sulfonate (compound 18)

mp: 150°–152° C.
ir: 3450, 2950, 1640, 1575, 1465 (cm$^{-1}$)

EXAMPLE 19

Sodium 7-isopropyl-3-n-pentylazulene sulfonate (compound 19)

mp: 168°–170° C.
ir: 3400, 2950, 2930, 2860, 1620, 1580, 1470, 1440, 1390, 1190, 1060 (cm$^{-1}$)

EXAMPLE 20

Sodium 7-isopropyl-3-(1'-R.S-1',5'-dimethyl-4'-hexene)-azulene sulfonate (compound 20)

mp: 113°–116° C.
ir: 3450, 2950, 1640, 1380, 1240, 1180 (cm$^{-1}$)

EXAMPLE 21

Sodium 7-isopropyl-3-(1'-R-1',5'-dimethyl-4'-hexene)-azulene sulfonate (compound 21)

mp: 114°–117° C.
ir: 3450, 2950, 1640, 1380, 1240, 1180 (cm$^{-1}$)

EXAMPLE 22

Sodium 7-isopropyl-3-(1'-S-1',5'-dimethyl-4'-hexene)-azulene sulfonate (compound 22)

mp: 115°–118° C.
ir: 3450, 2950, 1640, 1380, 1240, 1180 (cm$^{-1}$)

EXAMPLE 23

Sodium 7-isopropyl-3-benzylazulene sulfonate (compound 23)

mp: 250° C. (decomp.)
ir: 3450, 2950, 1640, 1560, 1530, 1460, 1420 (cm$^{-1}$)

EXAMPLE 24

Sodium 4-methoxy-3-methylazulene sulfonate (compound 24)

mp: 186°–188° C. (decomp.)
ir: 3400, 1600, 1570, 1540, 1460, 1370, 1270 (cm$^{-1}$)

EXAMPLE 25

Sodium 4-methoxy-3-ethylazulene sulfonate (compound 25)

mp: 60° C.
ir: 3400, 2950, 1600, 1570, 1540, 1450, 1370, 1270 (cm$^{-1}$)

EXAMPLE 26

Sodium 4-methoxy-3-propylazulene sulfonate (compound 26)

mp: 108°–110° C.
ir: 3450, 2910, 2850, 1600, 1570, 1530 (cm$^{-1}$)

EXAMPLE 27

Sodium 4-methoxy-3-butylazulene sulfonate (compound 27)

mp: 188°–190° C. (decomp.)
ir: 3450, 2950, 1600, 1570, 1530, 1460 (cm$^{-1}$)

EXAMPLE 28

Sodium 4-methoxy-3-pentylazulene sulfonate (compound 28)

mp: 189°–192° C. (decomp.)
ir: 3450, 2950, 1600, 1560, 1530, 1450 (cm$^{-1}$)

EXAMPLE 29

Sodium 4-methoxy-3-hexylazulene sulfonate (compound 29)

mp: 225°–228° C. (decomp.)
ir: 3450, 2900, 1650, 1560, 1520, 1460 (cm$^{-1}$)

EXAMPLE 30

Sodium 7-isopropyl-4-methoxy-3-methylazulene sulfonate (compound 30)

mp: 95°–97° C.
ir: 3450, 2950, 1650, 1540, 1280, 1180 (cm$^{-1}$)

EXAMPLE 31

Sodium 7-isopropyl-4-methoxy-3-ethylazulene sulfonate (compound 31)

mp: 108°–110° C.
ir: 3450, 2950, 1650, 1540, 1260, 1180 (cm$^{-1}$)

EXAMPLE 32

Sodium 7-isopropyl-4-methoxy-3-propylazulene sulfonate (compound 32)

mp: 188°–190° C.
ir: 3450, 2950, 1640, 1560, 1530 (cm$^{-1}$)

EXAMPLE 33

Sodium 7-isopropyl-4-methoxy-3-butylazulene sulfonate (compound 33)

mp: 166°–168° C.
ir: 3450, 2950, 1640, 1560, 1530, 1470 (cm$^{-1}$)

EXAMPLE 34

Sodium 7-isopropyl-4-methoxy-3-pentylazulene sulfonate (compound 34)

mp: 123°–125° C.
ir: 3450, 2950, 1650, 1520, 1260, 1010 (cm$^{-1}$)

EXAMPLE 35

3-methylazulene sulfonate acid aluminium salt (compound 35)

Five g. of sodium 3-methylazulene sulfonate is dissolved in water. To this solution, 2.73 g. of AlCl$_3$ in 40 ml. of water after filtration of the residue is added and stirred for 30 minutes at room temperature. The reaction mixture is adjusted to pH 4–4.5 by adding 10% NaOH. The precipitates formed are collected by filtration and washed with water and dried.

mp: over 250° C.
ir: 3400, 1630, 1580, 1395, 1140, 1040, 740 (cm$^{-1}$)
Al content: 13.96%

The following compounds (compound 36–38) are prepared in the same manner as example 36, from the corresponding sodium sulfonate derivatives.

EXAMPLE 36

3-ethylazulene sulfonic acid aluminum salt (compound 36)

mp: over 250° C.
ir: 3400, 2950, 1580, 1400, 1150, 1050, 750 (cm$^{-1}$)
Al content: 13.00%

EXAMPLE 37

7-isopropyl-3-methylazulene sulfonic acid aluminium salt (compound 37)

mp: over 250° C.
ir: 3400, 2950, 1420, 1150, 1040 (cm$^{-1}$)
Al content: 9.46%

EXAMPLE 38

7-isopropyl-3-ethylazulene sulfonic acid aluminium salt (compound 38)

mp: over 250° C.
ir: 3400, 2950, 1580, 1420, 1390, 1150 (cm$^{-1}$)
Al content: 10.58%

What is claimed is:

1. An azulene derivative of the formula:

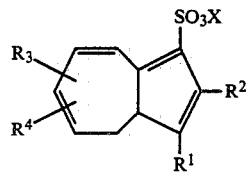

wherein $R^1$ is a lower alkyl, benzyl or

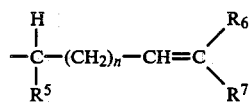

group, in which $R^5$, $R^6$, $R^7$ each represent H or a lower alkyl group and n is an integer of 1 or 2;

$R^2$ and $R^3$ each represent H or a lower alkyl group;

$R^4$ is H or an alkoxy group and X is Na or Al(OH)$_2$ with the proviso that $R^3$ and $R^4$ may be at any two of positions 4, 5, 6 and 7.

2. The compound according to claim 1 wherein $R^1$ is a lower alkyl group.

3. The compound according to claim 1 wherein $R^1$ is

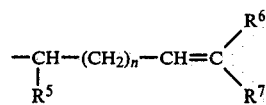

4. The compound according to claim 1 wherein $R^4$ is an alkoxy group.

5. The compound according to claim 1 wherein X is Na.

6. The compound according to claim 1 wherein X is Al(OH)$_2$.

7. Sodium 3-ethyl-7-isopropyl-azulene sulfonate 8. 3-Ethyl-7-isopropylazulene sulfonic acid aluminum salt.

9. A therapeutic composition comprising a pharmaceutically acceptable carrier and, as an active ingredient, a compound defined in claim 1 in an amount effective to treat peptic ulcer.

10. A therapeutic composition comprising a pharmaceutically acceptable carrier and, as an active ingredient, a compound defined in claim 1 in an amount effective to treat inflammation.

11. The azulene derivative according to claim 1 in which $R^3$ is at position 5,6 or 7 and $R^4$ is at position 4.

12. The azulene derivative according to claim 4 in which $R^3$ is at position 5,6 or 7 and $R^4$ is at position 4.

* * * * *